Figure 1:
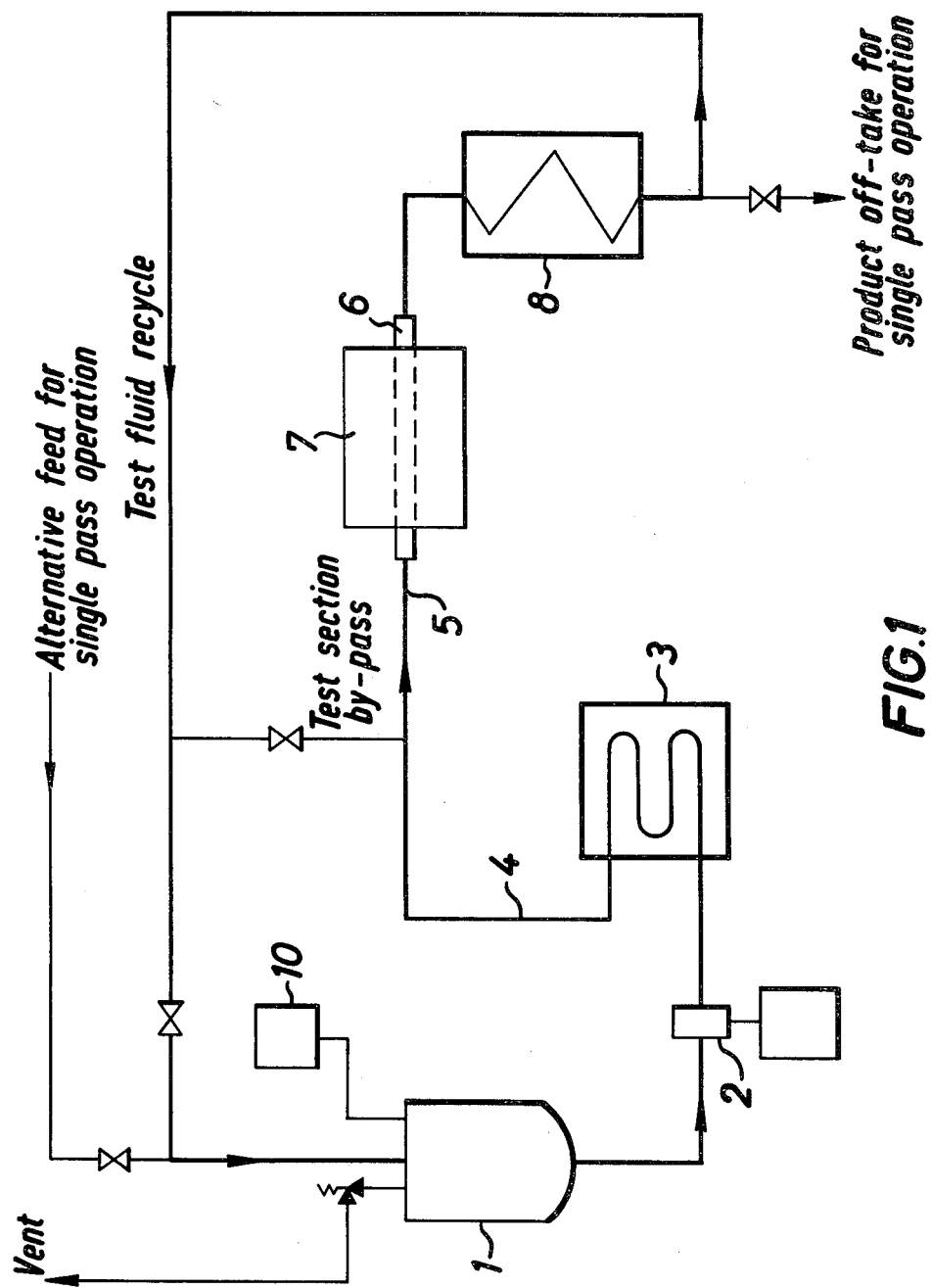

United States Patent [19]

Eyles et al.

[11] 4,176,544
[45] Dec. 4, 1979

[54] METHOD FOR DETERMINING FOULING

[75] Inventors: Martin K. Eyles, Addlestone; Graham L. Wagner, Walton-on-Thames, both of England

[73] Assignee: The British Petroleum Company Limited, London, England

[21] Appl. No.: 902,672

[22] Filed: May 4, 1978

[51] Int. Cl.² .............................................. G01N 17/00
[52] U.S. Cl. .................................... 73/61.2; 23/230 C
[58] Field of Search ........................ 73/61.2; 23/230 C

[56] References Cited

U.S. PATENT DOCUMENTS

| 3,141,324 | 7/1964 | Boies et al. | 73/61.2 |
| 3,552,189 | 1/1971 | Courvoisier et al. | 73/61.2 |
| 3,936,273 | 2/1976 | Powell | 23/230 C X |
| 4,044,605 | 8/1977 | Bratthäll | 73/61.2 |

Primary Examiner—Gerald Goldberg
Assistant Examiner—Joseph W. Roskos
Attorney, Agent, or Firm—Morgan, Finnegan, Pine, Foley & Lee

[57] ABSTRACT

A method for detecting the fouling tendency of a liquid which method comprises heating the liquid, adding to it a solution or suspension containing one or more inorganic and/or organic foulants to give an enhanced concentration of foulant in the liquid, passing the resulting liquid through a heated tubular test section and measuring the increase in pressure drop and/or the decrease in temperature across the test section over a period of time.

5 Claims, 3 Drawing Figures

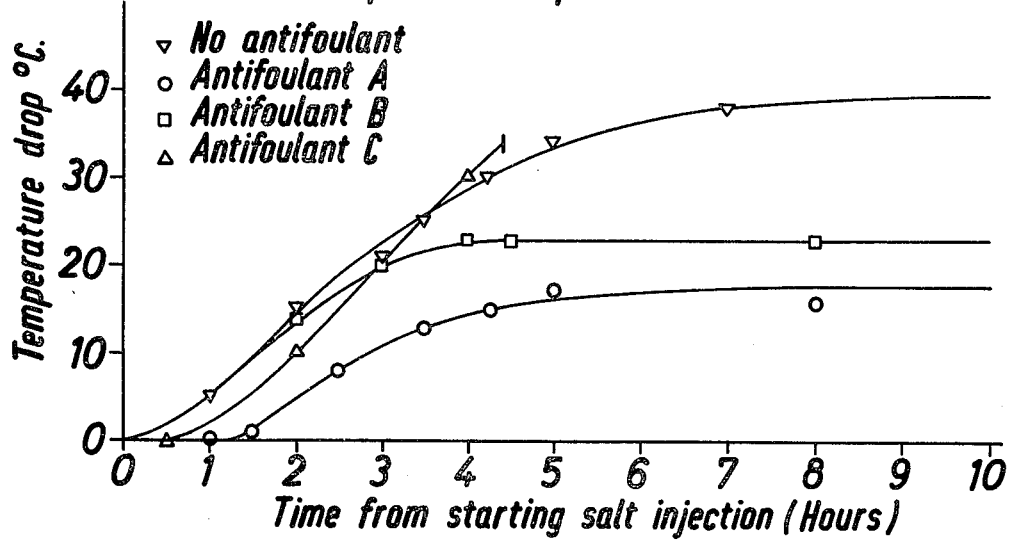
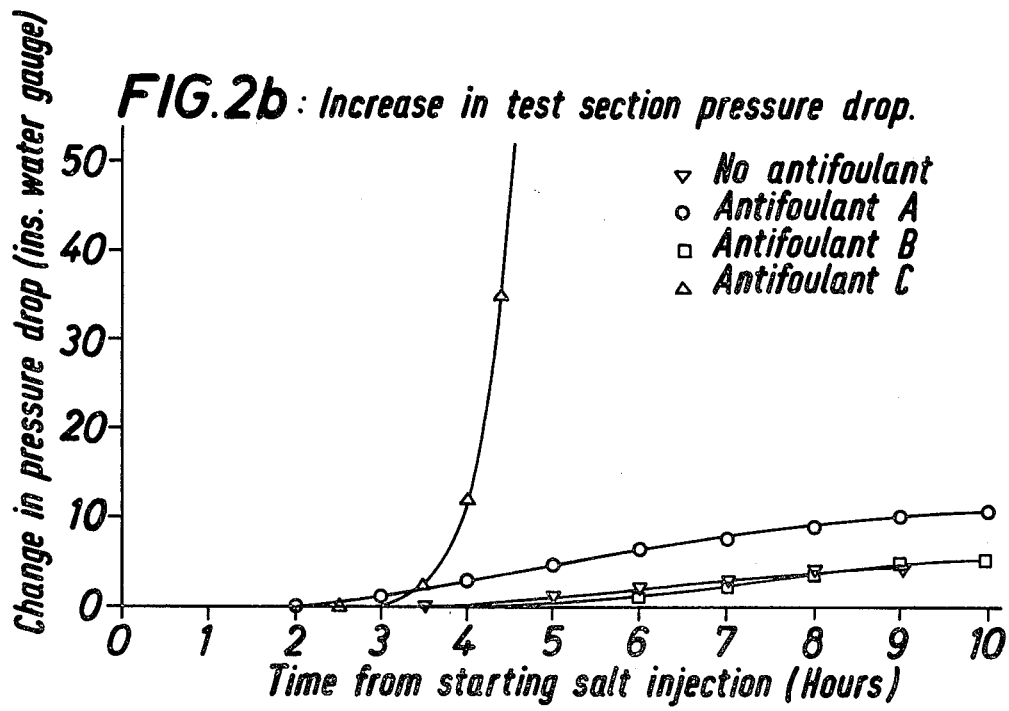

METHOD FOR DETERMINING FOULING

The present invention relates to a method for evaluating the fouling tendency of a heated liquid. In particular it relates to a method for evaluating the tendency of crude oil or petroleum fractions to foul the tubes of a heat exchanger.

The heat transfer in heat exchangers is often reduced during operation due to the fouling of the tube walls by deposition from the process stream. These fouled exchangers then operate at lower efficiencies and this often results in throughput reductions or even shut-downs for cleaning.

The most serious heat exchanger fouling problem within oil refineries usually exists in the crude oil distillation unit (CDU) preheat train where the hottest exchanger, i.e., the one immediately prior to the furnace, is particuarly susceptible to fouling by deposits which build up so quickly that frequent cleaning is required, sometimes as often as every four months.

In order that the distillation column inlet temperature is maintained so that fractionation efficiency and hence product quality is not lost, the heat input drop due to fouled exchangers has to be made up by increased firing of the furnace. With current fuel oil prices this can represent a significant increase in operating costs.

Analysis of deposits taken from these refinery exchangers indicated that both inorganic and organic deposition occurs, with the proportions of each varying from unit to unit. The inorganics are predominantly salts of iron (corrosion products), sodium (salt in the water associated with crude oil and from caustic soda injection) and calcium and magnesium (hardness salts in desalter water). A high proportion of these salts originate from the desalter where water dissolved in the crude oil leaving it can be as high as 0.3 percent weight. In addition, excess water carry-over occurs from time to time and it is this aqueous phase which contains the iron corrosion products, the hardness salts and the caustic being injected to prevent corrosion of the column overheads condenser. At the temperatures in these hottest exchangers, particularly at the outlet end, some of the water can be vaporised so that even soluble salts can be deposited out on the metal surfaces. Simultaneous lay-down of hydrocarbon polymers with their subsequent conversion to coke probably binds the inorganics into a hard deposit which is not readily flushed away by the flowing oil.

Frequent cleaning of heat exchangers is to be avoided for several reasons. Cleaning of the hottest CDU preheat exchangers usually requires the unit to be shut down or, if the exchangers are in parallel banks which can be isolated, the throughput to be reduced. Cleaning, particularly mechanical, requires a large maintenance effort and often lasts several days for each exchanger.

An alternative solution to the problem is the injection of an effective antifoulant into the crude oil stream before it enters the heat exchanger. Antifoulants are usually blends of additives in an organic solvent with injection levels in the range 5-30 ppm on crude. Because fouling is so complex and covers several different types and mechanisms, the active ingredients of antifoulants can be very varied. Examples of antifoulant types include dispersants, detergents, metal co-ordinators, antioxidants, film-formers, corrosion inhibitors and antipolymerants.

There is on the market a wide range of antifoulants. The assessment of antifoulants on a commercial unit is an expensive and time-consuming operation as a full trial would have to be run for several months. Some trials have even resulted in increased fouling. It is therefore desirable to carry out tests in the laboratory with the hydrocarbon stream and the antifoulants before any refinery trials are planned. Previously such tests have been relatively simple involving static heating of hydrocarbon samples and assessing sludge formation, etc. While these tests may give some indication of fouling tendencies, it is not possible to take account of the dynamics of the system under realistic flow and temperature conditions. In particular, methods must be devised whereby the refinery stream conditions themselves are reproduced on a laboratory scale to give meaningful results.

Specific laboratory equipment must be designed both to simulate the real fouling characteristics in a short period of time and to give the respective additives a preliminary screening prior to field testing. The initial laboratory screening will select the more effective additives for full scale testing, thus reducing the costs of such trials and preventing costly failures.

We have now discovered a method for evaluating fouling tendencies which realistically reproduces the process side conditions of refinery heat exchangers, more specifically the crude oil side of refinery CDU preheat exchangers.

Thus according to the present invention there is provided a method for detecting the fouling tendency of a heated liquid which method comprises heating the liquid, adding to it a solution or suspension containing one or more inorganic and/or organic foulants to give an enhanced concentration of foulant in the liquid, passing the resulting liquid through a heated tubular test section and measuring the increase in pressure drop and/or the decrease in temperature across the test section over a period of time.

Liquids which can pose fouling problems include crude oil, straight run distillates such as naphtha, kerosine and gas oil, and other hydrocarbon fractions.

For example, when the liquid is crude oil, the foulants added are salts of iron, sodium, calcium or magnesium or any combination thereof, depending on the fouling to be evaluated. They are preferably added in the form of an aqueous solution with a weight ratio approximating to the weight ratio of the actual fouling deposits.

The total addition of water should simulate the final water concentration of the stream the fouling tendency of which is being evaluated.

Temperature conditions are selected so that the liquid temperatures at the test section inlet and outlet are similar to those found in commercial operation.

The invention is illustrated with reference to the drawings accompanying the Provisional Specification wherein FIG. 1 is a simplified flow sheet of the apparatus for carrying out the method, FIG. 2a is a graph showing the decrease in test section oil outlet temperature plotted against time, and FIG. 2b is a graph showing the increase in test section pressure drop plotted against time.

The unit comprises a reservoir (1) for containing the test sample of hydrocarbon liquid, a circulation pump (2), a preheat section (3), a test section simulating the refinery process, and a cooler (8). The hydraulic pressure of the unit is produced and maintained by a pressurised inert gas which is metered and controlled by a regulator valve.

An important feature is an accurate metering system (10) whereby any liquid or liquid mixture may be added to the bulk circulating hydrocarbon fluid in both accurate quantities and at accurate rates.

The unit is capable of reproducing process variables such as conditions of temperature, velocity, heat input and pressure, thereby simulating and reproducing actual heat exchanger processes. The Reyonlds Numbers for the crude oil flow through the single heat exchanger tube can be varied such that the flow regime is turbulent, intermediate or laminar.

In operation the hydrocarbon liquid is placed in the feed pot (1) and recycled via the feed pump (2). These are facilities on the feed pot for both heating and stirring. The fluid is heated in the preheater (3) and line heaters (4 and 5) using electric windings, controlled by pipe wall temperatures, which are preset depending upon the nature of the fluid under test. In this way the fluid temperature can be carefully controlled to give either even uniform heating or a final high rate of heating just before entering the test section so that for temperature sensitive feedstocks, fouling does not occur before the test section.

The test section itself comprises a replaceable test piece tube (6) the internal surface of which has a standard finish. Each tube is used in only one test. The tube is 0.61 m long, 19 mm outside diameter and 6.5 mm bore with thermocouples fitted into grooves on the external surface. The tube is held within a furnace block (7) which is electrically heated and insulated to give a uniform heat flux along the length of the test piece. From the test section the fluid is passed to water coolers (8) where the temperature is rapidly reduced for recycle back to the feed pot.

The inorganic deposition which takes place commercially due to the presence of corrosion products, caustic and desalter water hardness salts in the hottest CDU preheat exchanger can be reproduced. In this way, the fouling characteristics of a given crude oil or the effectiveness of an antifoulant may be realistically determined within several days rather than months. This is achieved by adding to the recycling crude oil an aqueous mixture of sodium, iron and magnesium sulphates.

These metals are the ones which are found in commercial deposits in the largest quantities. The total concentration of the three metals added is 210 ppm with a weight ratio of 3:3:1 for Na:Fe:Mg. The total addition of water gives a final water concentration of 0.72 percent weight.

The rig conditions are set so that the oil temperatures at the test section inlet and outlet are those found in the commercial exchanger. The aqueous solution containing the inorganic salts mixture is then added at a fixed rate to the stirred feedpot from the metered injection system (10). Fouling occurs in the test piece and is indicated by both a reduction in the oil temperature at the outlet of the test piece, and an increase in the pressure drop across the test piece as shown in FIGS. 2a and 2b. Deposits obtained compare well with typical refinery deposits, and the procedure is fully reproducible. This method is also applicable to the comparison of antifoulants. The procedure is exactly repeated except the recommended dosage of additive is made to the crude oil charge. The effectiveness of the additive is indicated fully by the change in both the outlet temperature and pressure drop compared to the case without additive.

Further comparisons of antifoulant efficiencies may be made by calculating fouling factors for each antifoulant and relating them to those for the no antifoulant base case.

The following four examples illustrate runs with no antifoulant and with three antifoulants of widely differing effectiveness.

Example 1—no antifoulant
Example 2—antifoulant A—very good
Example 3—antifoulant B—good
Example C—poor In all four runs the same conditions were used. These are listed below:

| | | |
|---|---|---|
| Crude oil feedrate | liter/h | 25 |
| Crude oil linear velocity (in ¼ inch ID tube) | m/s | 0.2 |
| Reynolds Number (average in test section) | | 1500 |
| Test section oil inlet temperature | °C. | 130 |
| Test section oil outlet temperature at start of test | °C. | 220 |
| Average tube wall temperature | °C. | 300 |
| Unit pressure $N_2$ | bar | 11.5 |
| Sulphates solution injection rate | ml/h | 10 |
| Sulphates solution injected | ml | 40 |
| Crude oil | | Desalted Kuwait |
| Crude oil salt content | lb/bbl | 2/1000 |
| Crude oil antifoulant content | ppm | 30 |

The complete test procedure, exactly reproduced for each run, was as follows:

Five gallons of desalted Kuwait crude oil were charged to the feedpot (1). Where antifoulants were to be included, these were well mixed into the crude oil before charging. The feed pot contents were mixed by the stirrer during this charging operation. On completion, the pump was started and the oil recycled through the system. The feed pot temperature was raised to 45° C., the normal operating temperature. The pressure was then raised to 10 bar using nitrogen and vented to atmosphere. This flushed most of the air from the system. 100 ml of deionised water were added to the feed pot at a low rate while the pot contents were stirred and the oil recycled to increase mixing efficiency. This water was required to dilute the initial salt solution injected thereby preventing predeposition of salts in the preheaters and line heaters as the solubility of water in crude oil is increased. In tests with no added salts this also ensures that the crude oil contains the equilibrium water content.

The unit was then finally pressured to 11.5 bar in the feed pot with nitrogen. The corresponding pressure in the test section after the pump was 12 bar. The preheaters, line heaters and furnace were switched on and the unit lined out at the conditions given previously.

When the conditions were steady the aqueous solution containing the metal sulphates mixture was added at a constant rate of 10 ml/h through a micro-metering valve. The standard test allows for a total of 40 ml of solution to be added in four hours. Complete sets of readings were taken approximately half-hourly during this injection period, and every one-two hours afterwards. The pressure and temperature differences of the oil through the test section were continuously monitored on recorder charts. The runs were continued for up to 24 hours after beginning the injection, except for antifoulant C, where a high pressure drop necessitated early termination. The results from the four runs are shown in FIGS. 2a and b.

Except for antifoulant C, steady conditions were attained at approximately 10-12 hours from beginning the salt injection. For antifoulant C, the run was terminated before all the 40 ml of salt were added due to an excessive pressure drop indicative of a partial blockage. Differences in pressure drop for the other three runs were generally not significant.

From FIG. 2a, showing the drop in oil outlet temperature from the test section, the run with no antifoulant shows the highest overall drop and therefore the worst fouling. Both antifoulants A and B significantly reduced this temperature drop, with antifoulant A being the better. Antifoulant C gave no improvement to the temperature drop, and in addition caused a blockage in the test tube.

These results indicate that two independent fouling mechanisms occur under the conditions of the test. In one case, uniform deposition occurs along the test tube giving a steady reduction in outlet oil temperature, and in the other, heavy isolated deposition occurs where the effect on overall heat transfer is minimal, but a blockage is produced giving very high pressure drops. Antifoulant C obviously fails in both these cases.

In addition, some difference in the actions of antifoulants A and B may be indicated. The inorganic salts are injected for the first four hours, during which time the temperature drop for antifoulant B has reached the final value. However, for antifoulant A, only 80 percent of the total temperature drop occurs in the first four hours. This could merely result from the fact that as A is more effective, more salts remain in the oil available for deposition. Alternatively, this could show that A is very effective in stopping inorganic fouling, but not as effective in reducing fouling.

We claim:

1. A method for detecting the fouling tendency of a heated hydrocarbonaceous liquid which method comprises heating the liquid, adding to it a solution or suspension containing one or more inorganic and/or organic foulants to give an enhanced concentration of foulant in the liquid, passing the resulting liquid through a heated tubular test section and measuring the increase in pressure drop across the test section over a period of time.

2. A method for detecting the fouling tendency of a heated hydrocarbonaceous liquid which method comprises heating the liquid, adding to it a solution or suspension containing one or more inorganic and/or organic foulants to give an enhanced concentration of foulant in the liquid, passing the resulting liquid through a heated tubular test section and measuring the decrease in temperature across the test section over a period of time.

3. A method for detecting the fouling tendency of a heated hydrocarbonaceous liquid according to claim 2 which method comprises heating the liquid, adding to it a solution or suspension containing one or more inorganic and/or organic foulants to give an enhanced concentration of foulant in the liquid, passing the resulting liquid through a heated tubular test section, and measuring the increase in pressure drop as well as the decrease in temperature across the test section over a period of time.

4. A method according to any of the above claims 1-3 wherein the heated liquid is crude oil and the foulants added are salts of iron, sodium calcium or magnesium or any combination thereof.

5. A method according to any of the above claims 1-3 wherein foulant salts are added in the form of an aqueous solution with a weight ratio approximating to the weight ratio of actual fouling deposits.

* * * * *